United States Patent [19]
Dimmick, Sr., deceased et al.

[11] Patent Number: 5,844,677
[45] Date of Patent: Dec. 1, 1998

[54] APPARATUS AND ASSOCIATED METHOD FOR INSPECTING CONTAINERS FOR BULGES

[75] Inventors: Henry M. Dimmick, Sr., deceased, late of Butler, by Mary L. Dimmick, executrix; Mark F. Zanella, Sr., Cranberry Twp., both of Pa.

[73] Assignee: AGR International, Inc., Butler, Pa.

[21] Appl. No.: 985,051

[22] Filed: Dec. 4, 1997

[51] Int. Cl.[6] .................................................. G01N 21/00
[52] U.S. Cl. ........................................................ 356/240
[58] Field of Search ................................... 356/237–241;
  209/522, 524, 525, 526, 529, 530; 250/223 R,
  223 B; 348/91, 92, 128, 129, 130, 135;
  382/141, 142

[56] References Cited

U.S. PATENT DOCUMENTS

| | | | |
|---|---|---|---|
| 3,782,542 | 1/1974 | Scribner | 209/74 |
| 4,349,112 | 9/1982 | Wilks et al. | 209/538 |
| 4,731,649 | 3/1988 | Chang et al. | 358/106 |
| 5,591,462 | 1/1997 | Darling et al. | 425/173 |

*Primary Examiner*—Frank G. Font
*Assistant Examiner*—Michael P. Stafira
*Attorney, Agent, or Firm*—Arnold B. Silverman; Eckert Seamans Cherin & Mellott, LLC

[57] ABSTRACT

Apparatus for inspecting containers has a support arm for supporting and transporting the containers. The support arm has a pair of movable arms defining a gap and having a recess for engaging the exterior of the finish or neck of the containers. A light source directs lights onto the movable arms and a detector receives light passing through the gap between the movable arms. The detector emits a responsive electrical signal to a processor which determines whether the container has a bulge and whether it is a reject. The movable arms are so structured and positioned as to enlarge the gap when a bulge is present on the exterior of the finish or neck of the container. One or more support arms are preferably disposed within a container forming machine which forms blow molded resinous plastic containers. An associated method is disclosed.

25 Claims, 6 Drawing Sheets

APPARATUS AND ASSOCIATED METHOD FOR INSPECTING CONTAINERS FOR BULGES

BACKGROUND OF THE INVENTION

1. Field of the Invention

This invention relates to apparatus and an associated method for determining the presence of an undesired bulge in the neck or finish of containers and, more specifically, to such a system wherein optical, mechanical and electrical means combine to effect the desired inspection of plastic containers.

2. Description of the Prior Art

The term "bulge," as employed herein, refers to an undesired outward deformation in the neck or finish of a resinous plastic container and shall expressly include, but not be limited to, blow molded containers which have swelling, a bulge or a blow-out within the finish area of the neck.

It has been known in the manufacture of containers from polyethylene-based materials, such as polyethylene terephthalate (PET) and PEN, for example, that a variety of process control problems can occur. One such problem relates to the free form reheating and subsequent forming effect in the finish area on the exterior of the neck of the container. When too much heat is introduced, a bulge as defined hereinbefore can occur. Bulges interfere with the manufacturing process as well as the desired smooth transportation of the container throughout the manufacturing facility. Large bulges can create jamming in the forming machine and result in shut-downs as well as damage to the machine. Even relatively small defects which may be on the order of 0.02 inch oversize can cause problems if they pass through the forming machine as they can produce handling problems in other areas of the production line. This is particularly true with respect to those employing known systems which transport the containers by engaging them in the finish area and using air conveyors.

It has been known to attempt to address this problem through the use of imaging systems. See generally, U.S. Pat. No. 5,591,462. Such systems have been located inside the forming machine to monitor the finish region of products and remove defective containers. Such systems have limitations, however. One such limitation is encountered in systems that perform the inspection employing a single view of the containers. With a single view, only one cross-sectional diameter can be evaluated. While additional views can be added, there is a limited amount of available space within the forming machine and additional time is required to perform the additional inspection views. Such imaging is also inhibited by the forming machines transfer mechanisms which may limit or obstruct the view of the finish area of the container.

There remains, therefore, a need to provide an effective container finish inspection apparatus and associated method which will avoid these problems.

SUMMARY OF THE INVENTION

The present invention has met the above-described needs.

In the present invention, a combination of support arm mechanical engagement with the exterior of the container finish or neck coupled with the use of a light generating and sensing system and responsive conversion of the detective light to electrical signals which are introduced into processing means permits effective and rapid determination of whether the container neck has an undesired bulge.

The apparatus of the present invention in a preferred embodiment includes a support arm for supporting and transporting the containers. The support arm has a pair of movable arms or finish having a gap therebetween and defining a recess for engaging the exterior of the neck of the container. Light generating means for directing light onto the movable arms and detector means for receiving light passing through the gap are provided. Detector means generate a responsive electrical signal which is delivered to processing means for determining if a bulge is present. The movable arms are rotatable in opposite directions and, as a result, the gap is enlarged when a bulge is present thereby causing a greater amount of light to impinge on the detector means.

It is preferred that the inspection station be provided within the forming machine and that the light source be at a higher elevation than the support arm and that the detector be at a lower elevation.

A related method involves transporting a container on a support arm having a pair of movable arms with a gap defined therebetween. Light is caused to impinge on the movable arms with a container engaged in the recess defined therebetween. Light passing through the gap is monitored by the detector means which generates a responsive electrical signal which is delivered to the processing means for determining if the container is a reject due to the presence of a bulge. The rejected containers are separated from the containers which pass the inspection. A container sensor provides a signal to the processing means when a container is present in the inspection station.

It is an object of the present invention to provide an improved apparatus and associated method for inspecting blow molded containers for bulges.

It is another object of the present invention to provide such an inspection system which will have one or more such inspection systems for inspecting blow molded containers disposed within the forming machine.

It is a further object of the present invention to provide such an inspection system which employs container supporting and transporting means as an integral part of the inspection system.

It is a further object of the invention to provide such a system which is cost-effective, reliable and inspects containers at a high speed.

It is a further object of the present invention to provide such a system which may be employed effectively without relying on imaging systems.

These and other objects of the invention will be more fully understood from the following description of the invention on reference to the accompanying drawings.

DESCRIPTION OF THE PREFERRED EMBODIMENT

Figure 1:
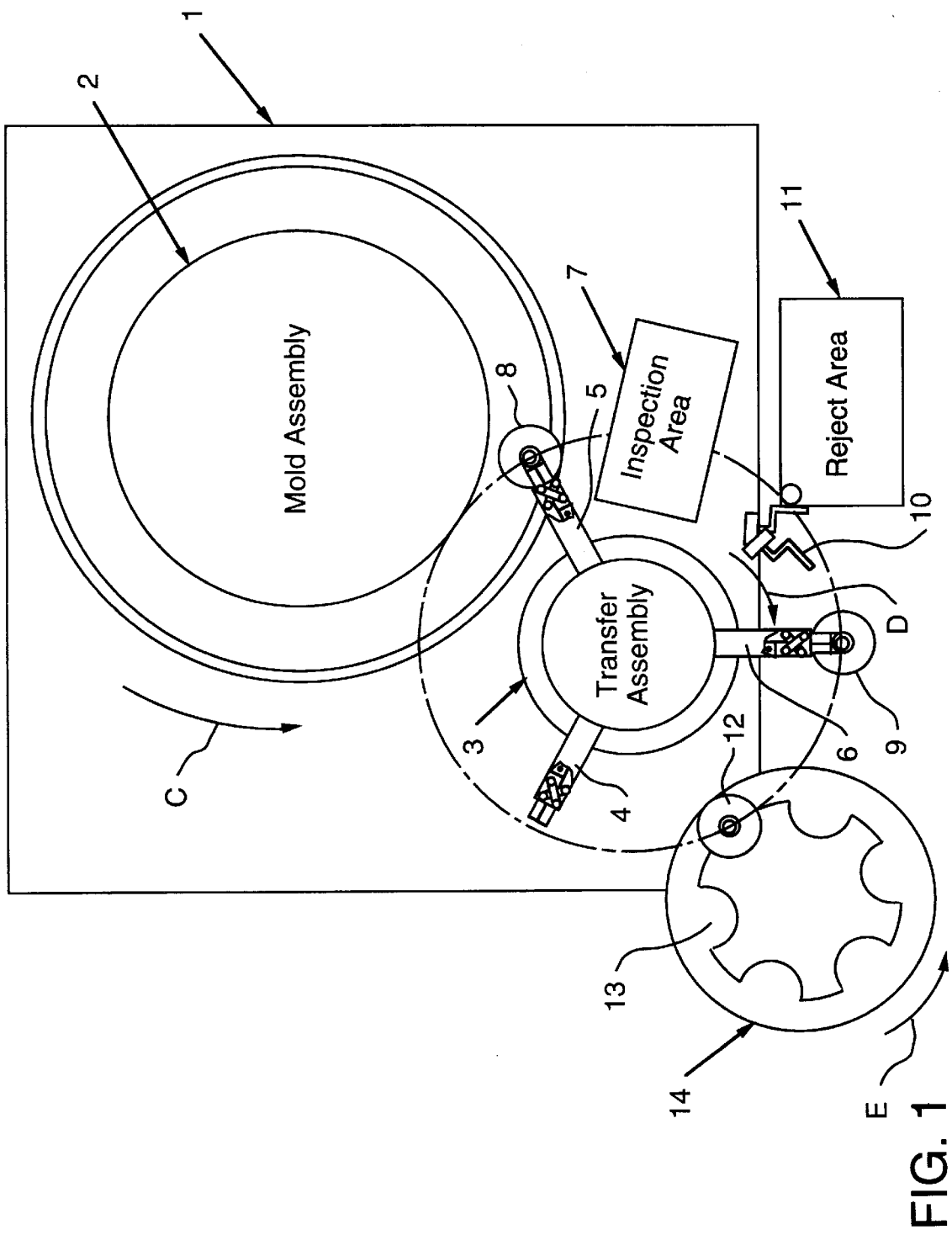
FIG. 1 is a schematic plan view of apparatus employing the inspection system of the present invention.

FIG. 1 shows a forming machine 1 of the present invention. The forming machine 1 contains the mold assembly 2 wherein the containers are made. The mold assembly 2 and the transfer assembly 3 which has a plurality of radially oriented container support arms 4, 5, 6 and the inspection station 7 are, in the preferred form, disposed within the forming machine 1. The containers emerging from the mold assembly move in a counterclockwise direction, as shown by arrow C, and are received in recesses in support arms 4, 5, 6 which are rotating in a clockwise direction as shown by arrow D. The apparatus will preferably have about 3 to 20 support arms 4, 5, 6. In this manner, containers, such as container 8, 9, pass sequentially through inspection station 7. Containers which emerge from inspection station 7, if they have a bulge, are removed by reject mechanism 10 and delivered to reject area 11 by suitable reject means known to those skilled in the art. Containers such as containers 9, 12, which are not rejected, are received in a recess, such as 13, for example, in outfeed wheel 14 which rotates in a counterclockwise direction indicated by arrow E.

Figure 2:
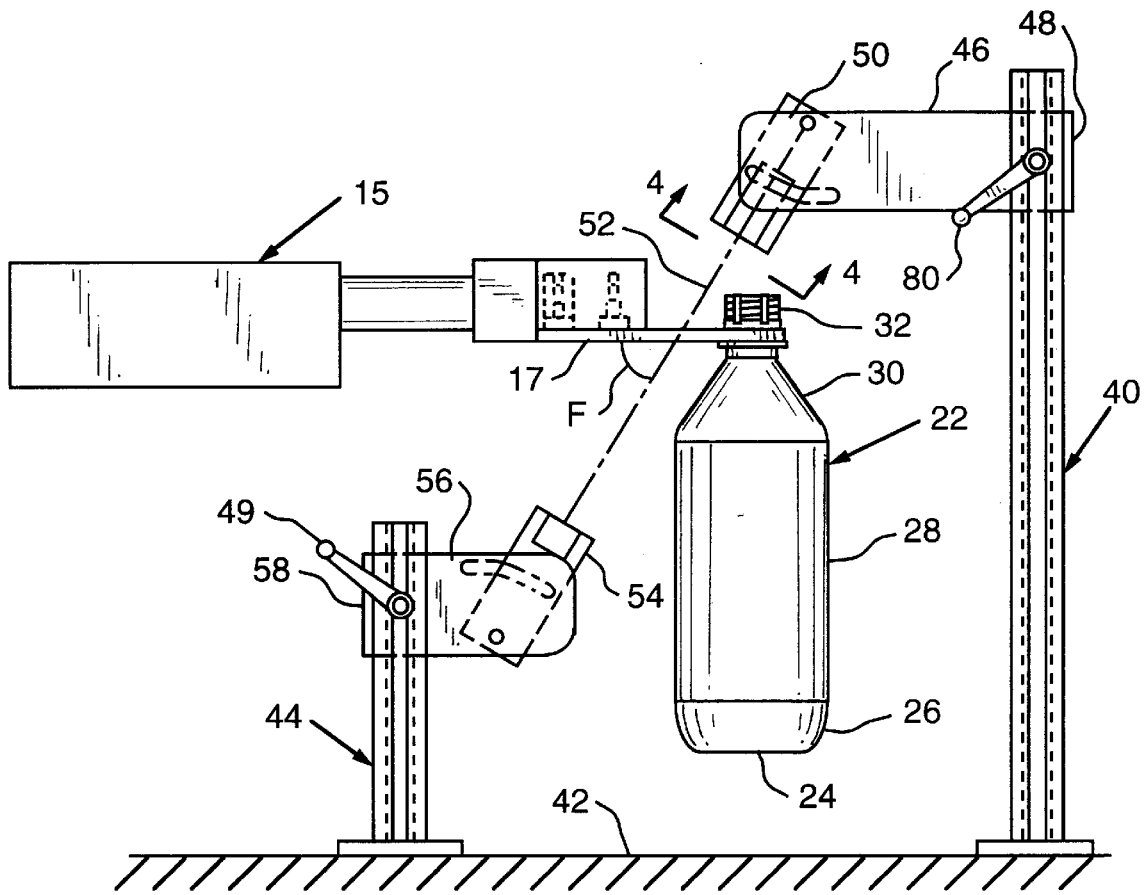
FIG. 2 is a partially schematic elevational view showing a preferred embodiment of the inspection apparatus of the present invention.
Figure 3:
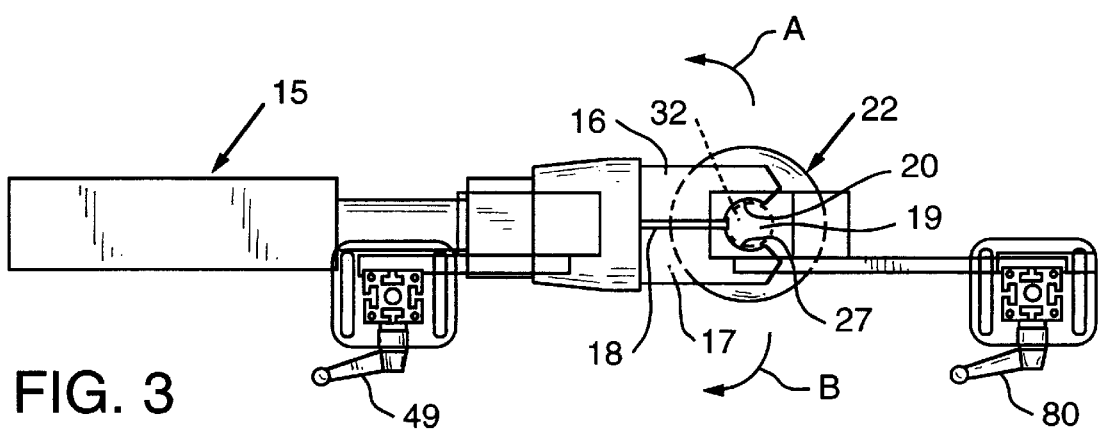
FIG. 3 is a plan view of the apparatus of FIG. 2.

Referring to FIGS. 2 and 3, there is shown a container support arm 15 which has a pair of movable arms 16, 17 which are mounted for rotational movement in opposed directions as indicated by arrows A and B. The movable arms 16, 17 define a gap 18 therebetween. A recess 19 defined by arcuate portions 20, 27, respectively, of movable arms 16, 17 are in intimate engagement with container 22. The container 22 is composed of a resinous plastic material and may be a polyethylene-based blow molded container. The container 22 has a base 24, an outwardly and upwardly diverging portion 26, a generally cylindrical portion 28, an inwardly and upwardly converging neck portion 30 and a finish portion 32 which has an appropriate closure receiving finish such as threads with an underlying outwardly projecting annular support rib which is engaged by the movable arms 16, 17 in order to transport the container 22.

Movable arm 16 is adapted to be pivoted about a pivot disposed to the left thereof and is adapted to be moved counterclockwise responsive to the presence of a container bulge in the portion of the recess 19 defined by surface 20. Similarly, movable arm 17 is adapted to be rotated in a clockwise direction responsive to the presence of a bulge in the container portion in recess 19 in contact with surface 27. Relative movement of movable arms 16, 17 serves to enlarge the gap 18 and, in a manner to be described hereinafter, results in more light impinging on the detector thereby indicating the presence of a bulge in the exterior of the container finish 32. As is known to those skilled in the art, containers of this general type have an exteriorly disposed finish portion 32 underlying the container mouth for securement of a closure to the container. Such finish region may, for example, have external threads. An external annular transport ring is generally spaced below the threads and may be engaged to support the container during transport in some types of handling equipment. In the present invention, the movable arms 16, 17 may engage the container between the finish and the transport ring. The neck portion 30 of the container extends generally from the middle of the transport ring to the upper part of the generally cylindrical portion. If desired, the movable arms may engage an upper part of the neck portion 30. Support post 40 is supported on floor member 42 as is support post 44. A bracket 46 has one portion 48 secured to the post 40 and has light generating means 50 which is oriented to direct a light ray or beam shown schematically as 52 generally angularly downwardly toward detector means 54 which are mounted on bracket 56 which in turn, has one end 58 fixedly secured to post 44. The area wherein the container supported by support arm 15 passes the movable arm 16, 17 through the light beam 52 is the inspection area. It will be appreciated that the amount of light passing through the gap is directly related to the mechanical action of the exterior neck of the container 22 and thereby depending upon the presence or absence of a bulge determines the amount of light passing through gap 18. The detector means 54, which may be a photosensor, a self-scanning array of photodiodes or a charge coupled device, for example, converts the received light into a corresponding output electrical signal which is delivered to processing means which determines whether the container has a bulge. The processing means, which may be a microcomputer, has stored voltage values relating to acceptable containers. If it does have a bulge of a magnitude which goes beyond specifications, the container is rejected and separated from containers which pass inspection.

Figure 4:
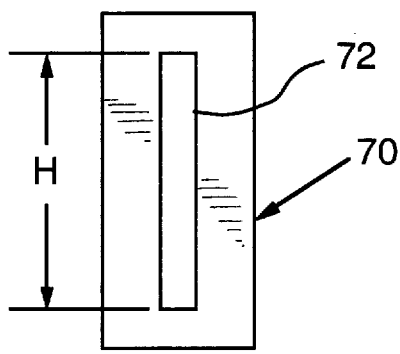
FIG. 4 is an example of a light beam employed in the present invention taken through 4—4 of FIG. 2.

In one embodiment of the invention, as shown in FIG. 4, light generating means 70 will generate an elongated generally rectangular light beam 72 with the cross-section of the light beam having its longitudinal dimension or height oriented generally perpendicular to axis 52. The smaller angle F (FIG. 2) between light beam 52 and the plane of removable arm 16, 17 is preferably about 50 to 75 degrees.

Handle means 80 permit relative adjustment of the position of support 46 on post 40. Similarly, handle means 49 permits adjustment of the position of support means 56 on post 44.

Figure 5:
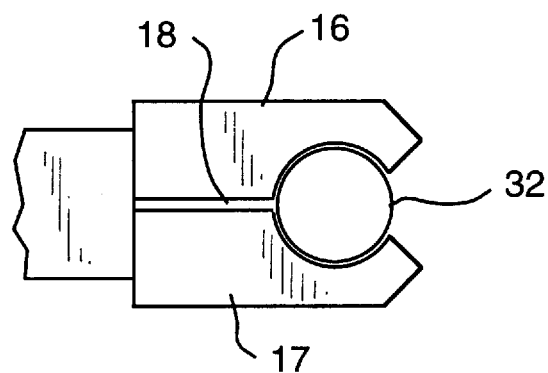
FIG. 5 is a fragmentary partially schematic plan view showing support arms and a container which does not have a bulge.

Referring to FIG. 5, a comparison, respectively, of a container finish 32 not having a bulge with a container 99 which does have a bulge will be considered. With solely the finish portion 32 of container being shown, a gap 18, which is normal gap, is established in FIG. 5. As a result, the movable arms 16, 17 remain in a normal position with the gap 18 being of the desired width.

Figure 6:
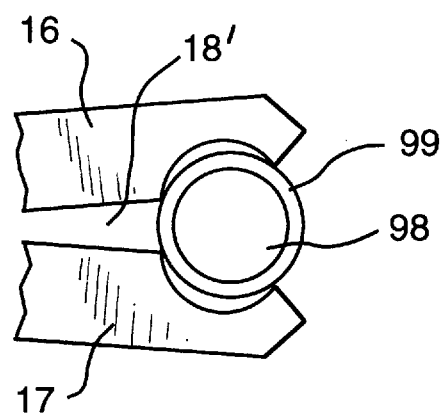
FIG. 6 is similar to FIG. 5, but shows a container with a bulge.

Referring to FIG. 6, a container finish 98 is shown as having a bulge 99 of substantially uniform radial projection. This causes an increased gap 18' with relative rotational movement of the movable arm 16, 17 in opposite directions. As a result, a greater quantity of light will pass through gap 18' than will through gap 18 thereby causing the detector 54 to receive more light and produce an electrical output voltage signal which is greater. This permits the processing means to effect a comparison between acceptable standard gap, such as 18 in FIG. 5, and that of the gap 18' of FIG. 6 to determine whether the bulge 99 exceeds specified limits and thereby results in rejection of the container.

Figure 7:
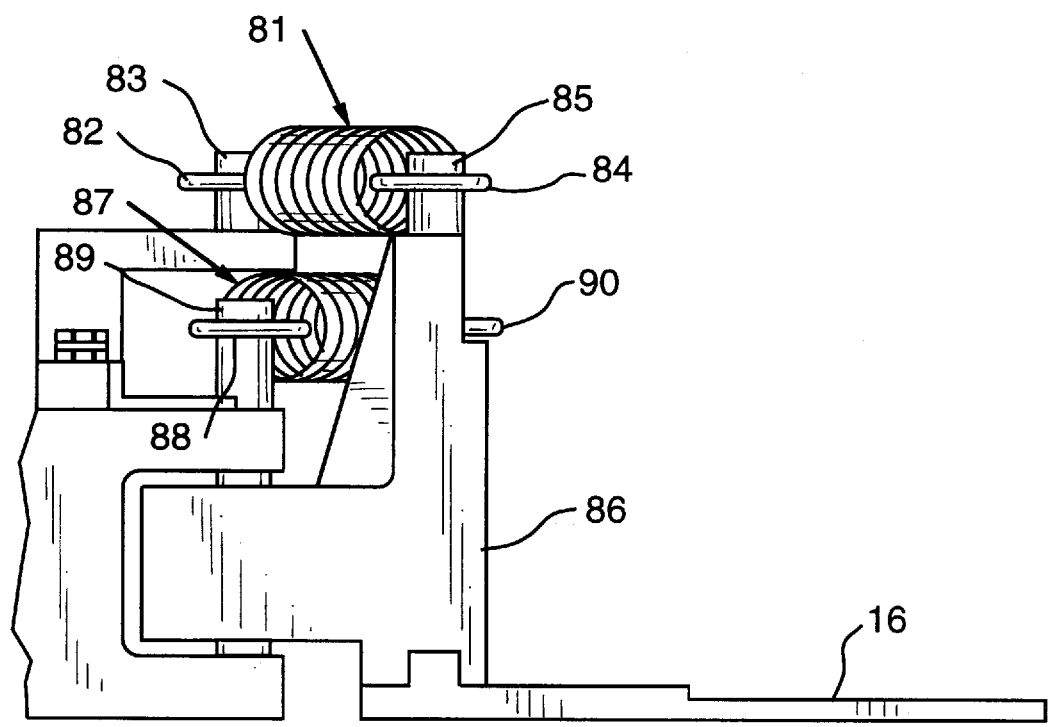
FIG. 7 is an elevational view of a container support arm.
Figure 8:
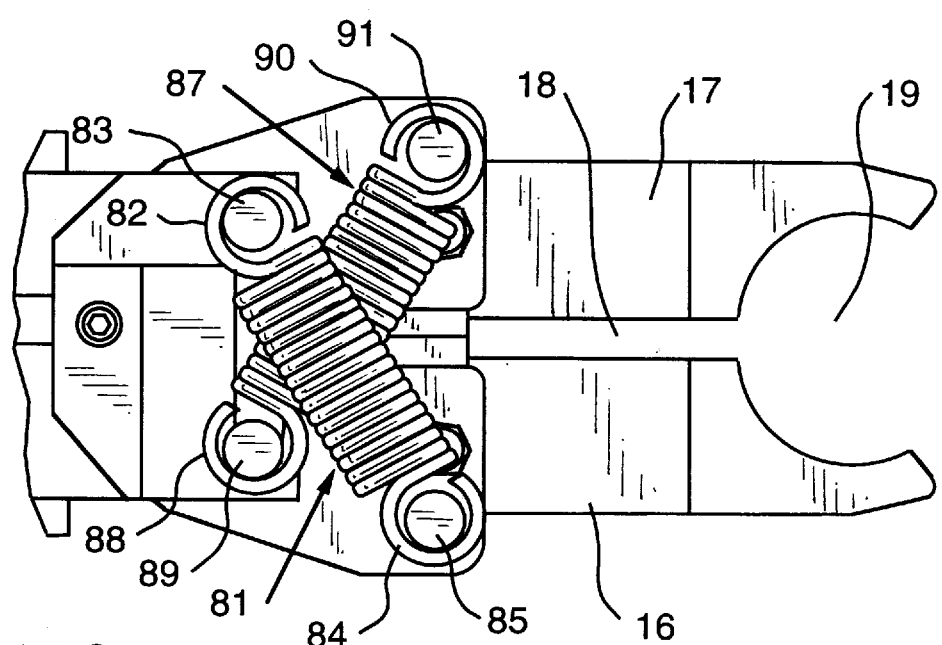
FIG. 8 is a top plan view of the support arm of FIG. 7 with the movable arms in closed position.
Figure 9:
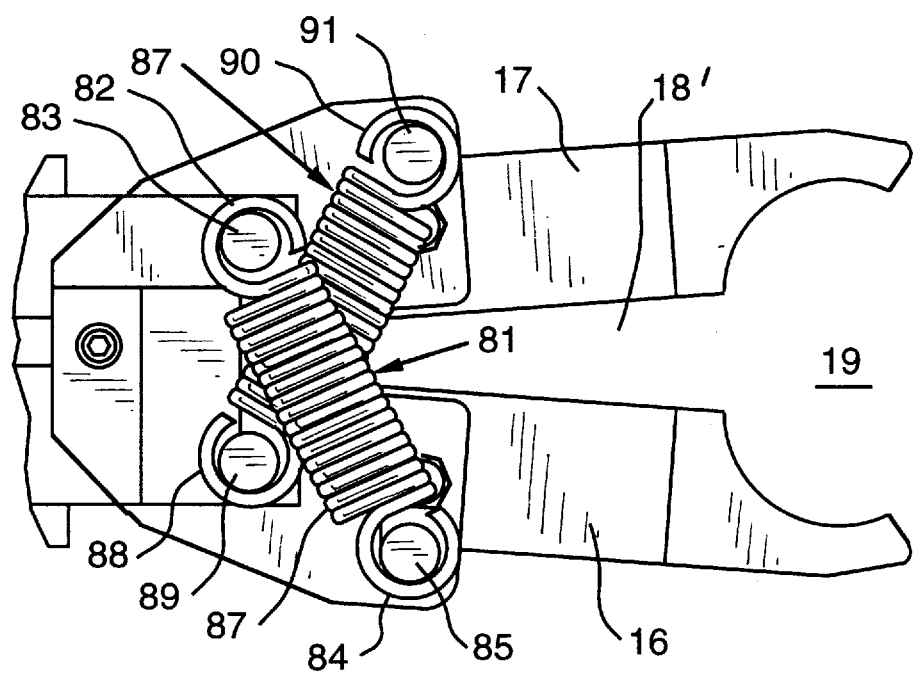
FIG. 9 is a top plan view of the support arm of FIG. 7 with the movable arms in an open position.

Referring to FIGS. 7 through 9, the preferred means for biasing movable arms 16, 17 of support arm 15 will be considered. Coil spring 81 has one end 82 secured to fixed post 83 and the other end 84 secured to post 85 which projects upwardly from connector 86 which is fixedly secured to movable arm 16. This construction causes movable arm 16 to be biased in the position shown in FIG. 8.

Similarly, spring 87 has one end 88 secured to fixed post 89 and end 90 secured to fixed post 91 which is fixedly connected to support arm 17 and urges it into the position shown in FIG. 8. FIG. 9 shows the support arm of FIG. 8 with gap 18' which indicates the presence of a container bulge.

Figure 10:
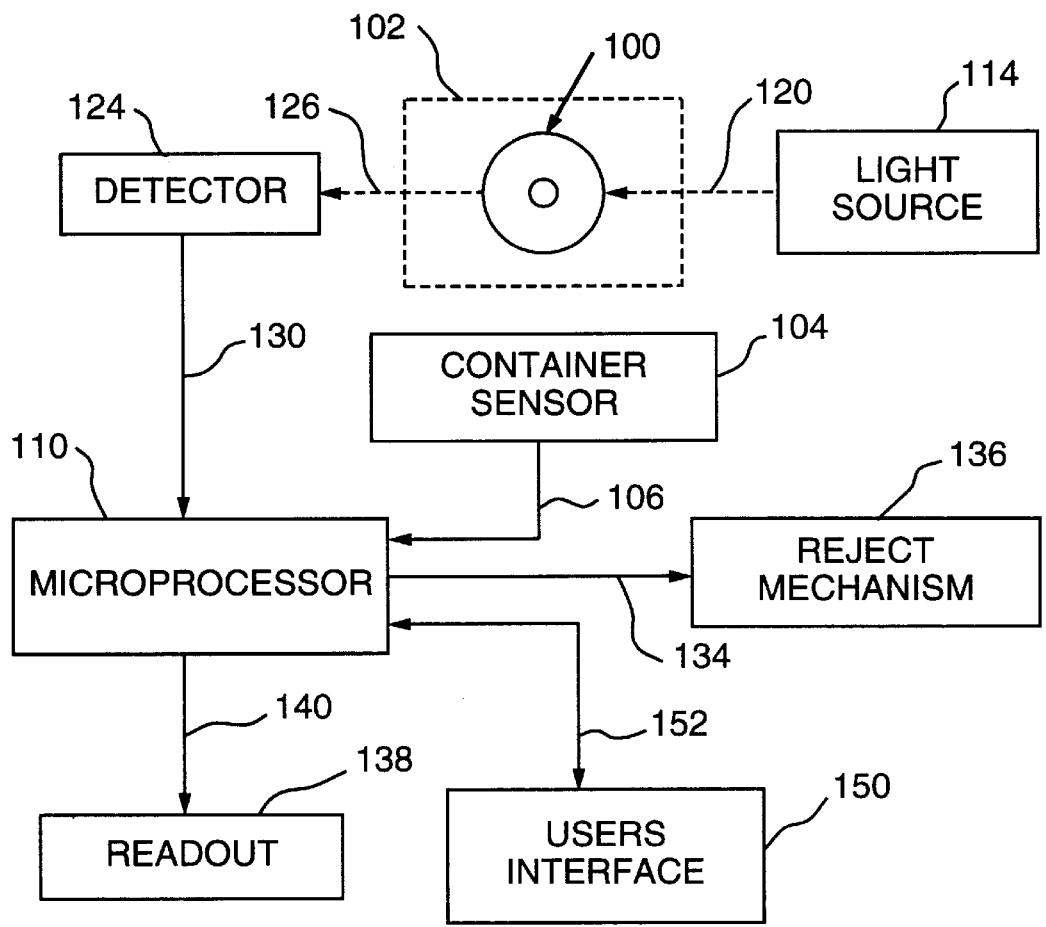
FIG. 10 is a flow chart of the present invention.

Referring to FIG. 10, it will be seen that a container 100 has been transported to an inspection station 102. A container sensor 104, which may be of the photoelectric, capacitive or ultrasonic type, emits a signal over lead 106 to microprocessor 110, which may be any suitably programmed general purpose computer, to indicate that an inspection cycle should be initiated. In a preferred practice of the invention, light source 114 is always on during operation of the system to cause it to emit light beam 120 which passes through the gap 18 (not shown in this view) between the movable arms 16, 17 when a container 100 is in the inspection station 102. The detector 124 receives that portion of the light beam 126 which passes through the gap between movable arms 16, 17 and emits a responsive electrical signal 130 to microprocessor 110.

Within the microprocessor 110, a comparison is made between stored values of gaps for each specific support arm which represent acceptable containers and what departures therefrom were required to conclude that a container is a reject due to the presence of a bulge. For convenience of disclosure, the inspection system of FIG. 1 is associated with a transfer mechanism delivering containers from the mold assembly 2 through inspection area 7. The system may, however, have on the order of about 3 to 20 support arms for delivering a like number of containers for inspection. If that difference is found, a signal is emitted by the microprocessor 110 over lead 134 to reject mechanism 136 which causes the container to be removed from the group of containers which are acceptable. Numerous reject mechanisms are known to those skilled in the art and need not be disclosed herein in detail. In general, such systems involve indexing and tracking a particular rejected container with the reject mechanism physically removing the rejected container due to mechanical contact with the reject mechanism. If desired, readout 138 which receives signals containing information as to performance of the inspection system from microprocessor 110 over lead 140 may be provided. For example, where it is desired a trend within a particular unit or support arm of the inspection system may be isolated to determine performance of certain portions of the forming apparatus or portions of the inspection apparatus. Similarly, user interface 150 provides for calibration and other input over lead 152 to microprocessor 110.

Figure 11:
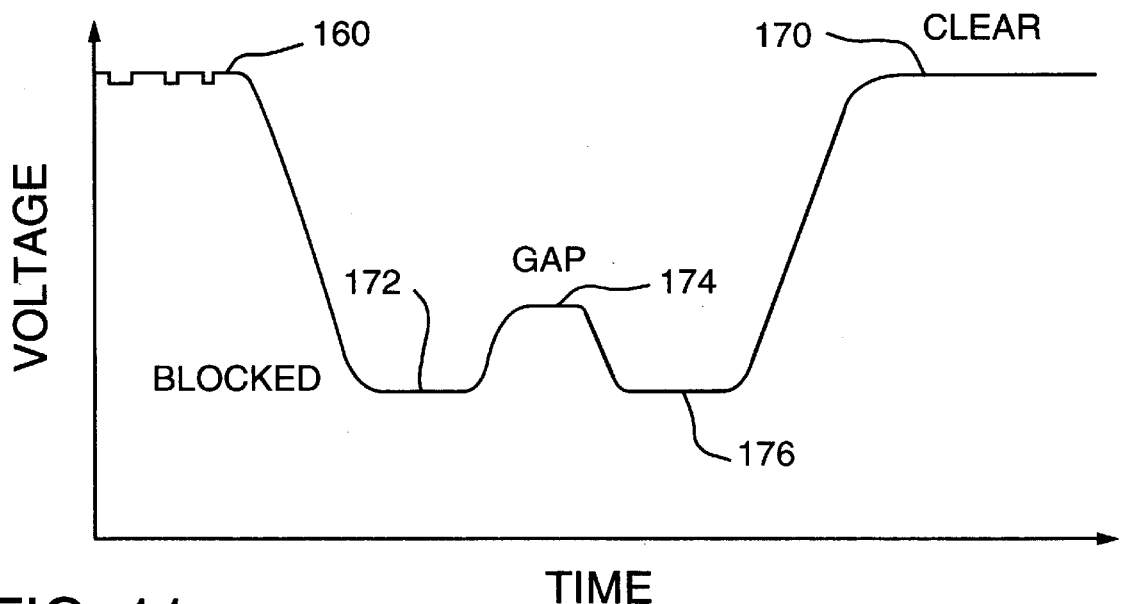
FIG. 11 is a plot of voltage versus time during a cycle of operation of the inspection system.

If desired, a portion of the readout 138 may be displayed on a screen or provide hard copy having information, such as that shown in FIG. 11, which is a plot of voltage taken at 174 versus time. The voltage level received by microprocessor 110 has an upper value at positions 160, 170 when no support arm is present in the inspection station 102. It decreases to having a blocked value 172 when the movable arms 16, 17 solid portion completely interrupts the light beam and a reading 174 which is of great importance in respect of the inspection as it determines the amount of the gap opening. After passing the gap 174, once again, the light is completely blocked 176 by other movable arms after which the voltage is ramped to the clear position 170 as no support arm 16, 17 is present in the inspection station.

In the method of the present invention, a container 22 is supported on a support arm which has a pair of oppositely rotatable movable arms 16, 17 which define a gap 18 therebetween. The movable arms 16, 17 have a recess 19 which support the container finish or neck and transport the container 22, supported in this manner, to an inspection station wherein a light beam 52 is caused to impinge on the movable arms 16, 17 and gap 18 therebetween with the light passing through the gap 18 being measured by a detector 54 which converts the received light into a responsive signal related to the size of gap opening. The voltage signal is delivered to processor means which determine through comparison with standard information stored therein whether a reject container is present or not. This method is preferably carried on within a blow molding forming machine so as to effect rapid accurate and complete inspection for bulges in such containers.

It will be appreciated that the present invention provides a method and apparatus for inspecting for undesired bulges on the exterior finish portion of blow molded containers. Such inspection may be accomplished within the forming machine by a single inspection unit of the present invention having a plurality of container supporting movable arms. A single microprocessor may be employed to control each of the them. This is accomplished without requiring imaging and without being burdened by the limited space available within the forming machine.

Whereas particular embodiments of the invention have been described above for purposes of illustration, it will be appreciated by those skilled in the art that numerous variations of the details may be made without departing from the invention as described in the appended claims.

We claim:

1. Apparatus for inspecting containers comprising
   a support arm for supporting and transporting said containers,
   said support arm having a pair of movable arms having a gap formed therebetween and defining a recess for engaging the exterior of the neck or finish of said containers,
   light generating means for directing light onto said movable arms,
   detector means for receiving light passing through said gap and generating responsive electrical signals, and
   processing means for receiving said signals from said detector means for determining if said container is a reject.

2. The inspection apparatus of claim 1 including
   said movable arms being relatively rotatable to alter said gap size.

3. The inspection apparatus of claim 2 including
   said movable arms being structured to have a larger said gap therebetween when said container has a bulge than when it does not.

4. The inspection apparatus of claim 3 including
   said apparatus having an inspection station wherein said support arm supporting said containers will receive said light, and
   said inspection station being disposed within a container forming machine.

5. The inspection apparatus of claim 4 including
   said light generating means being adapted to establish a light beam of greater width than said gap on said support arm.

6. The inspection apparatus of claim 3 including
   reject means for discarding a said container which is rejected as a result of the presence of a bulge in the container neck.

7. The inspection apparatus of claim 4 including transport means for moving said support arms in a path through said inspection station.

8. The inspection apparatus of claim 4 including said apparatus having container sensor means for determining the presence of a container in said inspection station and emitting a responsive signal to said processing means, and said processing means responsive to receive of said container present signal initiating an inspection of said container.

9. The inspection apparatus of claim 1 including said movable arms being structured to be an intimate engagement with said neck or finish exterior of blow molded resinous plastic containers.

10. The inspection apparatus of claim 9 including said light generating means being disposed at a higher elevation than said support arms to generate a light beam angularly downwardly.

11. The inspection apparatus of claim 10 including said detector means being disposed at a lower elevation than said support arm.

12. The inspection apparatus of claim 5 including said light generating means being adapted to establish a light beam on said support arm of a lesser width than the width of said arms when in relative closed position engaging the neck or finish of a non-reject container.

13. The inspection apparatus of claim 1 including said processing means having stored information related to the gap for non-reject containers for each said pair of movable arms.

14. The inspection apparatus of claim 4 including said apparatus having about 3 to 20 support arms.

15. The inspection apparatus of claim 2 including biasing means for urging said movable arms into relative closed position.

16. The inspection apparatus of claim 15 including said biasing means having a coil spring for each said movable arm.

17. A method for inspecting a container comprising providing a support arm having a pair of relatively movable arms defining a gap therebetween for engaging the exterior of the neck or finish of said containers, introducing said support arm supported container into an inspection zone, imposing a light beam on said support arm, receiving the light passing through said gap by detector means which emit a responsive electrical signal corresponding to the degree of gap opening, and determining from said electrical signal whether said container is a reject or not.

18. The inspection method of claim 17 including employing said method to inspect for bulges in said container neck or finish.

19. The inspection method of claim 18 including effecting by containers having a bulge within said container neck or finish relative opposite rotation of said movable arms to enlarge said gap.

20. The inspection method of claim 17 including removing containers which have been rejected due to the presence of a bulge in the neck or finish area.

21. The inspection method of claim 17 including effecting said inspection within a container-forming machine.

22. The inspection method of claim 21 including employing said method on blow molded resinous plastic containers.

23. The inspection method of claim 21 including impinging said light onto said movable arms from a position above said movable arms and receiving light passing through said gap by said detector means at a lower elevation than said support arm.

24. The inspection method of claim 18 including establishing said light beam with a generally vertically oriented rectangle having its maximum dimension oriented generally perpendicular to the beam of light travel.

25. The inspection method of claim 24 including employing said method with a plurality of support arms within said forming machine.

\* \* \* \* \*